United States Patent [19]

Proudian

[11] 4,315,435
[45] Feb. 16, 1982

[54] DUAL SCAN ULTRASONIC SCANNER

[75] Inventor: Andrew Proudian, Chatsworth, Calif.

[73] Assignee: Second Foundation, Chatsworth, Calif.

[21] Appl. No.: 164,316

[22] Filed: Jun. 30, 1980

[51] Int. Cl.³ ............................................ G01N 29/04
[52] U.S. Cl. ........................................ 73/628; 73/641; 128/660
[58] Field of Search .................. 73/641, 620, 625, 626, 73/628, 632; 128/660; 310/322, 334, 335, 336

[56] References Cited

U.S. PATENT DOCUMENTS

| | | | |
|---|---|---|---|
| 4,143,554 | 3/1979 | Nagy et al. | 73/641 |
| 4,185,501 | 1/1980 | Proudian et al. | 73/641 |
| 4,245,511 | 1/1981 | Soldner | 128/660 |

Primary Examiner—Stephen A. Kreitman
Attorney, Agent, or Firm—Wayne Willenberg

[57] ABSTRACT

An ultrasonic scanner for use in medical diagnosis which produces two different types of scans. The scanner includes a housing carrying one or more ultrasonic transducers which traverse an arcuate path. A first reflector is positioned within the arcuate path to intercept ultrasonic waves and converge them at a point beneath the scanner in order to produce a skin centered sector scan, which is useful for viewing through small acoustic windows such as intercostal regions. A pair of reflectors, one of which is positioned horizontally with respect to the first reflector and the transducers, are utilized to form a wide aperture sector scan which diverges upon exiting the scanner housing. The wide aperture scan is useful for scanning spaces such as the abdomen which include relatively few obstructions.

16 Claims, 6 Drawing Figures

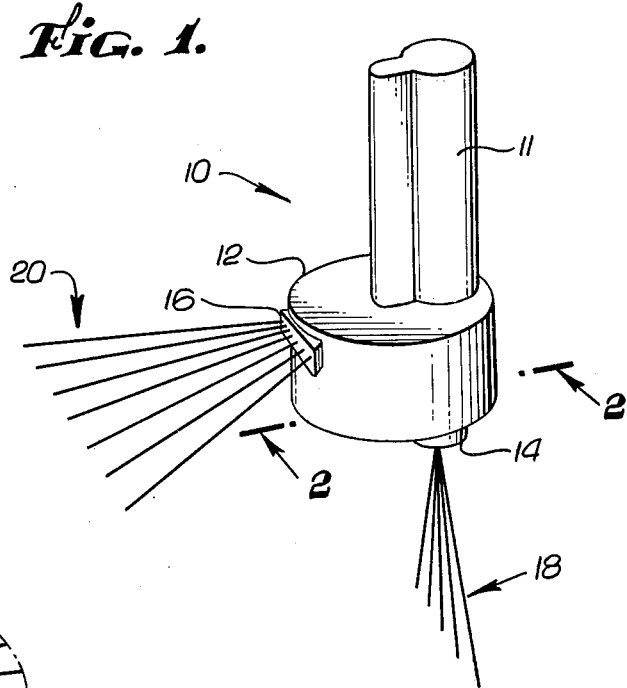
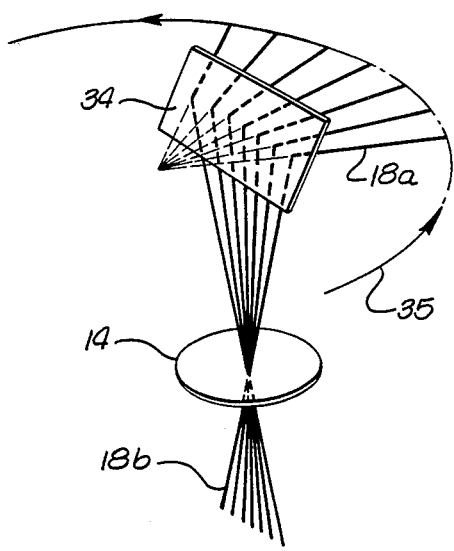
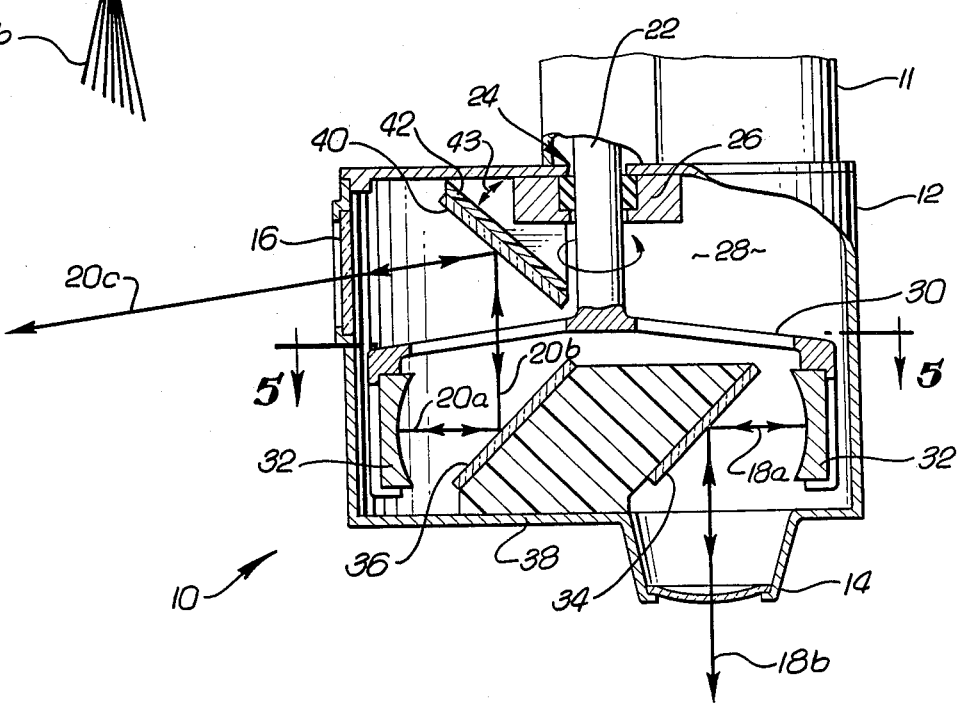

DUAL SCAN ULTRASONIC SCANNER

BACKGROUND OF THE INVENTION

1. Field of the Invention

This invention relates to the field of ultrasonic scanners, and in particular to dynamic imaging scanners. Ultrasonic scanners operate by directing ultrasonic sound waves at objects and detecting echoes or reflections from the objects in order to obtain images. Ultrasonic scanners of this type are particularly useful for medical applications.

2. Description of the Prior Art

Cross-sectional echography is a commonly used technique for producing two dimensional images of cross-sectional slices of the human anatomy. Dynamic two dimensional echography or imaging refers to such techniques and devices whereby such images are produced sequentially at a frame rate sufficiently high to enable dynamic visualization of moving organs.

Several variations of ultrasonic scanners are disclosed in U.S. Pat. Nos. 2,483,821 to Firestone; 3,269,173 to von Ardenne and 3,362,501 to Lenahan; German Patent Nos. 2,601,559; 2,529,112 and 1,001,977; and in U.S.S.R. Patent No. 184,000. In addition, ultrasonic scanners are discussed in Kossoff et al, *Ultrasonic Two-Dimensional Visualization for Medical Diagnosis*, J.A.S.A., November 1968, pages 1310-1317 and in Bacon, *New Developments in Ultrasonic Transducers and Their Applications to Nondestructive Testing*, Nondestructive Testing, May-June 1961, pages 184-187. One of the differences between various dynamic imaging ultrasonic scanners is the geometry of the cross-sectional image which is produced by the scanner. In one popular type of scanner, referred to as sector scanners, the imaged cross section consists of a sector of a circle having an included angle typically ranging from 60 degrees to 90 degrees. As much as possible, the center of the sector scan, i.e., the central point from which the sector diverges, is placed at or near the patient's skin so as to permit viewing of the human anatomy through small acoustic "windows" which are located in various intercostal spaces. These acoustic windows are locations on the human body which are not directly above sound reflecting structures such as ribs, sternum or other bone tissue, and which also provide paths between the skin and the organs of interest which are entirely in soft tissue and/or fluid, since ultrasound will not penetrate air (e.g., in the stomach), lung tissue or bone. Such acoustic windows are found mostly in intercostal spaces, i.e., between ribs. Thus, the utility of a sector scanner lies in its ability to produce a narrow image at or near an acoustic window (i.e., at or near the skin) which fans out below the acoustic window. Without such a fanning characteristic, the effective field of view of the scanner would be severely restricted by the ribs or other interfering structures. The requirements of sector scanners are fulfilled in phased array type scanners, such as that shown in German patent No. 2,529,112, and in mechanical scanners such as that shown in U.S. Pat. No. 4,143,554, issued to Nagy, et al and assigned to the same assignee as the present invention.

The geometry of the above type of scanners, hereinafter skin centered sector scanners, has certain drawbacks. As a consequence of the location of the scan center at or near the skin (which is required to permit imaging through small acoustic windows), the width of the image at small penetration depths, i.e., near the sector origin or center, is necessarily small. Although this is desirable when the scan must pass through a small acoustic window, organs or anatomical features located near the skin will be incompletely imaged with this type of scanner. In some areas of the anatomy such as the lower abdomen, the acoustic windows are not small and the sector geometry of the skin centered sector scanners unnecessarily limits the field of view. In such scanning situations, a sector scanner with the scan center spaced from the skin is desirable. If the scan center is spaced from the skin, the sector will have a substantial width at the skin line, thus providing a wide field of view near the skin. Such scanners, hereinafter wide aperture sector scanners, are available commercially.

Heretofore, either a skin centered sector scanner or a wide aperture sector scanner was chosen depending upon the type of scanning problem encountered. However, there are many instances in which it is desirable to obtain both a skin centered and a wide aperture scan of a given organ or anatomical structure. In order to provide a complete scanning capability, two separate instruments are therefore required, resulting in increased cost and examination time.

Accordingly, it is a primary object of the present invention to provide a sector scanner which incorporates both a skin centered sector scan and a wide aperture sector scan. It is a further object of the present invention to provide such a scanner which is simple in both design and operation. It is a further object of the invention to provide a scanner which is capable of using a single set of ultrasonic transducers for use with both the skin centered and wide apertured sector scans.

BRIEF DESCRIPTION OF THE DRAWINGS

In the drawings:

FIG. 1 is a perspective view of the scanner of the present invention;

FIG. 2 is a cross sectional view of the scanner along line 2—2 of FIG. 1;

FIG. 3 is a scan diagram of the skin centered scan portion of the present invention;

DETAILED DESCRIPTION OF THE DRAWINGS

Figure 4:
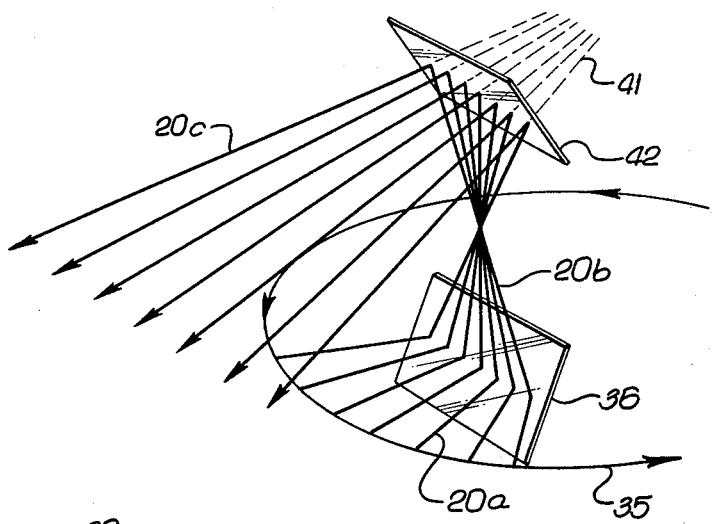
FIG. 4 is a scan diagram of the wide aperture scan portion of the present invention.

Referring to FIG. 1, the scanner 10 includes a housing having an upper generally cylindrical portion 11 and lower generally cylindrical portion 12. A skin centered scan exit window 14 is located on the bottom of the portion 12. Although the exit window 14 may simply be a flat membrane, the preferred embodiment of the invention utilizes a protuberance for the exit window in order to space the remainder of the bottom of the scanner 10 away from the patient. The window 14 can be made of a variety of materials, including but not limited to plastics (polycarbonates and polyethylene) and hard rubber. Located on the side of the portion 12 is a wide aperture sector scan window 16, which can be made of the same material as the window 14.

The scanner of FIG. 1 produces a skin centered sectors can 18 which exits from the window 14 and a wide aperture sectors can 20 which exits from the window 16. When the scanner 10 is placed so that the window 14 contacts the patient's skin, the sector scan 18 will be very narrow near the skin surface, while the sector scan 20 will be relatively wide at the skin surface. By providing both types of scan sectors simultaneously, the scanning operation is much more efficient.

Referring now to FIG. 2, the scanner 10 includes a rotatable shaft 22 which extends from the upper portion of the housing 11 into the lower portion 12 through an aperture 24. The aperture 24 is provided with a seal structure 26 to prevent the leakage of a fluid 28 which is contained within the lower portion 12. The shaft 22 is driven by a motor (not shown) located in the upper portion 11. The function of the fluid 28 is to provide an increased scan sector angle and is fully described in U.S. Pat. No. 4,143,554 issued on Mar. 13, 1979 to Nagy, et al, the disclosure of which is herein incorporated by reference.

Attached to the bottom of the shaft 22 is a horizontal circular transducer support plate 30. The support plate 30 has one or more transducers 32 attached to and extending downward from its end. The transducers 32 are coupled to leads (not shown) which pass through the support plate 30 and into the shaft 22, which has a hollow center. The leads transmit information between the transducers 32 and processing equipment used in conjunction with the scanner 10. As the shaft 22 is rotated, the transducers 32 traverse an arcuate path within the housing portion 12. The transducers 32 generate signals which are directed towards the center of the housing portion 12. A support block 38 of attentuating material such as polyethylene is secured to the bottom of the portion 12 below the shaft 22 and support plate 30. A pair of reflectors 34 and 36 are secured to the support block on opposite sides thereof. The reflector 34 is used to form a skin centered scan sector 18, and the reflector 36 is used in conjunction with the formation of the wide aperture scan sector 20. The support block 38 serves to absorb any ultrasonic waves which pass through the reflectors 34 and 36, thereby preventing interference.

The operation of the skin centered scan portion of the present invention is essentially identical to that of the scanner disclosed in the aforementioned U.S. Pat. No. 4,143,554. The present invention combines the operation of the scanner therein described with a wide aperture scan sector scanner without requiring the use of any additional transducers. As the transducers 32 traverse an arcuate path 35 within the housing portion 12, they will alternately be positioned opposite the mirrors 34 and 36. As the transducers scan across the reflector 34, a skin centered scan as shown in FIG. 3 will be produced. Ultrasonic waves generated by the transducer 32 follow a path 18a until they strike the reflector 34. The emerging waves, denoted 18b, form a planar sector scan.

In order to generate a wide aperture sector scan, ultrasonic waves 20a from the transducers 32 are reflected from the reflector 36 along a path 20b and strike an upper reflector 40. A support structure 42 of attenuating material serves to locate the reflector 40. The ultrasonic waves reflect off the reflector 40 and follow a path 20c through the window 16. The formation of the wide aperture sector scan is shown in FIG. 4. Although the ultrasonic waves are initially directed towards the center of the housing portion 12, they are redirected by means of the reflectors 36 and 40 so as to exit through the side of the housing portion 12. The position of the reflectors is chosen so that the ultrasonic waves appear to be coming from a point located behind the reflector 40 at the intersection of dashed lines 41. Generally, the positions of the reflectors will be chosen so that the effective focus point will be coincident with the axis of rotation of the shaft 22, although this is not critical. The important factor in the positioning of the reflectors 36 and 40 is that they operate so that the waves 20c emanating from the windows 16 have diverged to a sufficient extend by the time they reach the patient. In the preferred embodiment of the invention, the waves 20c will diverge prior to or immediately upon striking the reflector 40 (i.e., the effective point of focus is behind the reflector 40). However, proper functioning may also be obtained with a point of focus which is in front of the reflector 40, as the waves 20c will still diverge from that point before reaching the patient.

Figure 5:
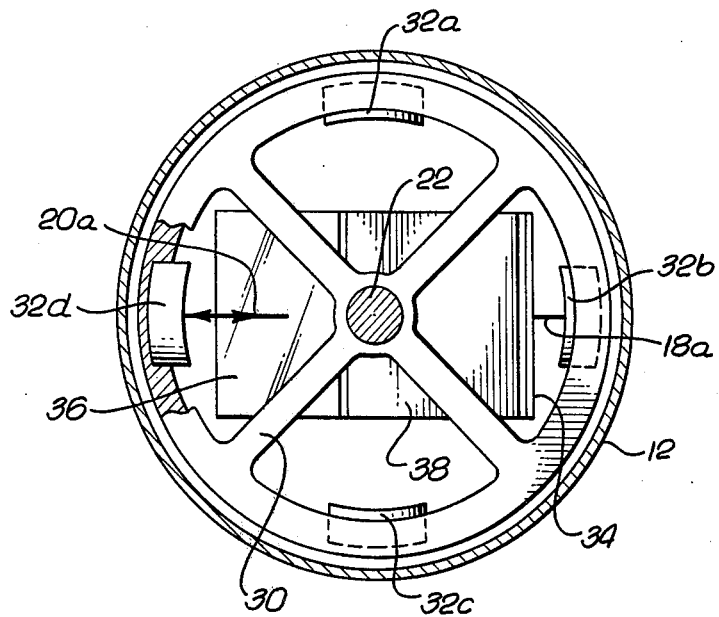
FIG. 5 is a top sectional view of the scanner of the present invention taken along lines 5—5 of FIG. 2.

Referring now to FIG. 5, it can be seen that the same set of transducers can be used to generate both the skin centered sector scan and the wide aperture sector scan. Assuming, for example, that four transducers 32a-d are employed, the transducer 32a will be utilized to generate the wide aperture scan while the transducer 32c will be simultaneously utilized to generate the skin centered scan. The activation of the transducers 32 can be controlled by means of suitable electronic switching so that information received from the scans can be properly analyzed (i.e., so that information relating to the skin centered scan will not be confused with information relating to the wide aperture scan).

In the scanner of the present invention, the support plate 30 may have a disc shape and be made of a material which is transparent to ultrasonic waves, thereby permitting the waves reflected off the reflector 36 to pass through the plate 30 and strike the reflector 40. One material relatively transparent to sound is thin polyethylene. Alternatively, the support plate 30 can have openings cut into it, as shown in FIG. 5, so that the sound can get through to and from the upper reflector 40. In addition, although the reflector 40 is shown as being mounted in a fixed position, it could be made adjustable along the direction of an arrow 43 (FIG. 2) so as to permit the user to control the position of the scan center.

Figure 6:
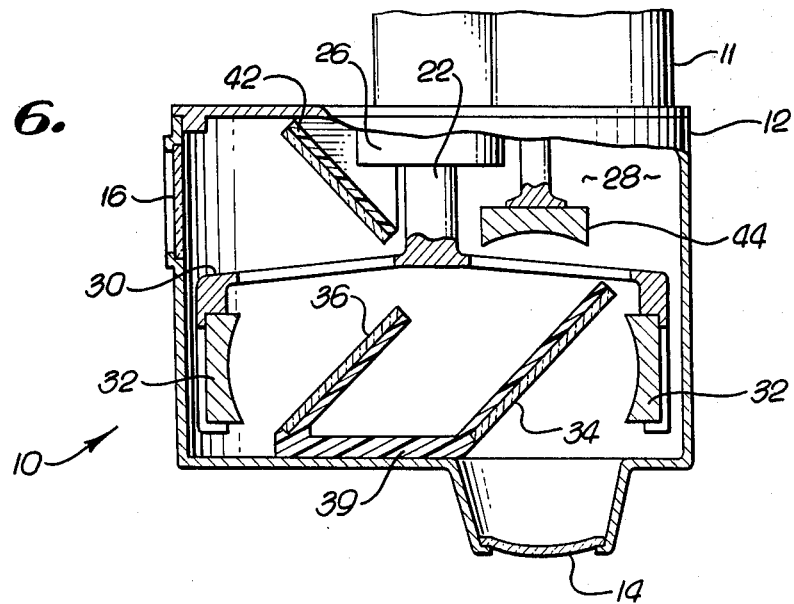
FIG. 6 is a side sectional view of an alternate scanning arrangement which includes an additional transducer that permits obtaining M-mode or pulse doppler echo information.

Referring now to FIG. 6, an alternative embodiment of the present invention includes a stationary transducer 44 positioned above the reflector 34 (and a thin support 39) so as to generate a wave in line with one of the waves 18b. The reflector 34 in this case is partially reflecting rather than completely reflecting, so as to enable ultrasonic waves produced by the transducer 44 to radiate through the reflector 34 in coincidence with one of the lines of the sector scan, thus permitting simultaneous M-mode or pulse doppler echo information to be obtained in perfect registration with the sector scan lines. Details of the use of an additional transducer in this matter are discussed thoroughly in the aforementioned U.S. Pat. No. 4,143,554.

In summary, the present invention is directed to a dual scan ultrasonic scanner which provides both a skin centered sector scan and a wide aperture sector scan while requiring only one set of transducers. Although the transducers face inward, the design of the present invention enables an outward scan to be generated. Although the invention has been described in terms of preferred embodiments, numerous modifications and variations within the scope of the invention will occur to those skilled in the art. In particular, the number and operation (e.g., duty cycle) of the transducers could be varied depending upon the type of scans desired. In some instances, all of the transducers which are used to generate the skin centered sector scan may not be needed to generate the wide aperture sector scan. The present invention therefore should not be limited by the foregoing description but only to the scope of the appended claims.

I claim:

1. A dual scan ultrasonic scanner comprising:
a housing;
one or more ultrasonic transducers movably mounted within the housing;
drive means for causing the transducer(s) to traverse an arcuate path within the housing;
first reflector means positioned within the arcuate path for receiving and reflecting ultrasonic waves from the transducer(s), wherein said first reflector means are oriented with respect to the ultrasonic waves to cause the ultrasonic waves to scan across the first reflector means and are reflected to converge at a point a preselected distance in front of the first reflector means; and
second reflector means positioned within the arcuate path for receiving and reflecting ultrasonic waves from the transducers, wherein the second reflector means are oriented with respect to the ultrasonic waves to cause the ultrasonic waves to diverge as they exit from the housing.

2. The scanner of claim 1 wherein said first reflector means comprises a single reflector surface angled to direct ultrasonic waves out of the bottom of the housing and said second reflector means comprises at least two reflector surfaces angled to direct ultrasonic waves out of the side of the housing.

3. The scanner of claim 2 wherein said second reflector means includes a lower reflector which receives ultrasonic waves from the transducers and is horizontally spaced from the first reflector means and an upper reflector which receives ultrasonic waves from the lower reflector and directs the ultrasonic waves out of the scanner.

4. The scanner of claim 3 wherein the orientation of said second reflector means is adjustable to control the location of the scan emanating from the second reflector means.

5. The scanner of claim 3 wherein the first reflector means and the lower reflector of the second reflector means are attached to a support block of attenuating material, said attenuating material absorbing ultrasonic waves.

6. The scanner of claim 1 wherein said drive means includes a transducer support to which the transducers are attached and a rotatable shaft connected to the transducer support substantially perpendicular thereto.

7. The scanner of claim 1 wherein said housing includes first and second exit windows, said first exit window allowing ultrasonic waves from the first reflector means to exit the housing and said second exit window allowing ultrasonic waves from the second reflector means to exit the housing.

8. The scanner of claim 7 wherein said exit windows are made of plastic.

9. The scanner of claim 7 wherein said exit windows are made of rubber.

10. The scanner of claim 7 wherein said first exit window includes a protruding section located on the bottom of the housing for spacing the housing from a subject being scanned.

11. A dual scan ultrasonic scanner comprising:
a housing having a bottom exit window and a side exit window;
a rotatable shaft passing through the top and into the interior of the housing;
a transducer support plate connected to the shaft substantially perpendicular thereto;
one or more ultrasonic transducers attached to the end of the support plate and facing inward toward the rotational axis of the shaft;
first reflector means, located within the housing between the transducers and the rotational axis of the shaft, for directing ultrasonic waves from the transducers through the bottom exit window; and
second reflector means, located within the housing between the transducers and the rotational axis of the shaft, for directing ultrasonic waves from the transducers through the side exit window.

12. The ultrasonic scanner of claim 11 wherein: said first reflector means comprises a single reflector which causes reflected ultrasonic waves from the transducers to converge at a point located near the bottom exit window to thereby provide a skin centered scan; and
said second reflector means comprises a lower reflector horizontally spaced from the first reflector means and angled to reflect ultrasonic waves upward and an upper reflector spaced above the lower reflector and angled to reflect ultrasonic waves from the lower reflector out of the side exit window in a diverging fashion.

13. The ultrasonic scanner of claim 12 wherein:
the transducers extend below the support plate and are substantially horizontally spaced with respect to the first reflector means and the lower reflector;
said upper reflector is located above the support plate; and
the support plate permits the passage of ultrasonic waves.

14. The ultrasonic scanner of claim 13 wherein the support plate includes one or more apertures to enable the passage of ultrasonic waves.

15. The ultrasonic scanner of claim 13 wherein the support plate is made of a material which is substantially transparent to ultrasonic waves.

16. The ultrasonic scanner of claims 1 or 11 wherein the first reflector means is partially reflective and further including stationary transducer means positioned within the housing to direct ultrasonic waves through the first reflector means along a path substantially coincident with ultrasonic waves reflected from the first reflector.

* * * * *